United States Patent
Lee et al.

(10) Patent No.: US 8,052,638 B2
(45) Date of Patent: Nov. 8, 2011

(54) ROBUST MULTI-LAYER BALLOON

(75) Inventors: Jeong S. Lee, Diamond Bar, CA (US); Fortino Vasquez Flores, Fallbrook, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/479,700

(22) Filed: Jun. 5, 2009

(65) Prior Publication Data

US 2010/0130926 A1    May 27, 2010

Related U.S. Application Data

(63) Continuation-in-part of application No. 12/324,425, filed on Nov. 26, 2008.

(51) Int. Cl.
*A61M 31/00* (2006.01)
(52) U.S. Cl. .................................. 604/103.06
(58) Field of Classification Search .............. 604/103.06
See application file for complete search history.

(56) References Cited

U.S. PATENT DOCUMENTS

| | | | |
|---|---|---|---|
| 4,952,357 A | 8/1990 | Euteneuer | |
| 5,112,304 A | 5/1992 | Barlow et al. | |
| 5,195,969 A | 3/1993 | Wang et al. | |
| 5,207,700 A | 5/1993 | Euteneuer | |
| 5,270,086 A | 12/1993 | Hamlin | |
| 5,290,306 A | 3/1994 | Trotta et al. | |
| 5,312,430 A | 5/1994 | Rosenbluth et al. | |
| 5,358,486 A | 10/1994 | Saab | |
| 5,447,497 A | 9/1995 | Sogard et al. | |
| 5,478,320 A | 12/1995 | Trotta | |
| 5,499,980 A | 3/1996 | Euteneuer | |
| 5,512,051 A | 4/1996 | Wang et al. | |
| 5,556,383 A | 9/1996 | Wang et al. | |
| 5,587,125 A | 12/1996 | Roychowdhury | |
| 5,613,979 A | 3/1997 | Trotta et al. | |
| 5,620,649 A | 4/1997 | Trotta | |
| 5,755,690 A | 5/1998 | Saab | |
| 5,769,817 A | 6/1998 | Burgmeier | |
| 5,797,887 A | 8/1998 | Rosen et al. | |

(Continued)

FOREIGN PATENT DOCUMENTS

EP    0420488    3/1991

(Continued)

OTHER PUBLICATIONS

U.S. Appl. No. 12/324,425, filed Nov. 26, 2008.

(Continued)

*Primary Examiner* — Nicholas Lucchesi
*Assistant Examiner* — Jason Flick
(74) *Attorney, Agent, or Firm* — Baker Botts LLP

(57) ABSTRACT

A multilayer balloon catheter is formed to have an inner layer and an outer layer, where the outer layer is adapted to resist shredding and premature rupture. The outer layer is formed of a material having a glass transition temperature that is lower than the transition or melting temperature of the inner layer. By forming the balloon on a mold at a temperature between the glass transition temperature of the outer layer and the glass transition or melting temperature of the inner layer, the outer layer will undergo a thermal relaxation that will alleviate some of the axial orientation of the polymer chains that develop during the formation of the multilayer balloon. This relaxation leads to a resistance to shredding when the balloon is expanded during operation.

16 Claims, 3 Drawing Sheets

U.S. PATENT DOCUMENTS

| | | | |
|---|---|---|---|
| 5,833,657 A | 11/1998 | Reinhardt et al. | |
| 5,879,369 A | 3/1999 | Ishida | |
| 5,908,406 A | 6/1999 | Ostapchenko et al. | |
| 6,004,289 A | 12/1999 | Saab | |
| 6,004,339 A | 12/1999 | Wijay | |
| 6,059,751 A | 5/2000 | Ostapchenko et al. | |
| 6,071,266 A | 6/2000 | Kelley | |
| 6,086,556 A | 7/2000 | Hamilton et al. | |
| 6,124,007 A | 9/2000 | Wang et al. | |
| 6,132,824 A | 10/2000 | Hamlin | |
| 6,136,258 A | 10/2000 | Wang et al. | |
| 6,146,356 A | 11/2000 | Wang et al. | |
| 6,171,278 B1 | 1/2001 | Wang et al. | |
| 6,242,063 B1 | 6/2001 | Ferrera et al. | |
| 6,265,016 B1 * | 7/2001 | Hostettler et al. | 427/2.11 |
| 6,358,227 B1 | 3/2002 | Ferrera et al. | |
| 6,416,494 B1 | 7/2002 | Wilkins | |
| 6,500,148 B1 | 12/2002 | Pinchuk et al. | |
| 6,585,688 B2 | 7/2003 | Ferrera et al. | |
| 6,620,127 B2 | 9/2003 | Lee et al. | |
| 6,620,128 B1 | 9/2003 | Simhambhatia | |
| 6,645,422 B2 | 11/2003 | Jung, Jr. et al. | |
| 6,673,302 B2 | 1/2004 | Wang et al. | |
| 6,695,809 B1 | 2/2004 | Lee | |
| 6,756,094 B1 | 6/2004 | Wang et al. | |
| 6,796,958 B2 | 9/2004 | Chen et al. | |
| 6,796,960 B2 | 9/2004 | Cioanta et al. | |
| 6,835,189 B2 | 12/2004 | Musbach et al. | |
| 6,875,197 B1 | 4/2005 | Simhambhatia et al. | |
| 6,911,038 B2 | 6/2005 | Mertens et al. | |
| 6,946,092 B1 | 9/2005 | Bertolino et al. | |
| 6,951,675 B2 | 10/2005 | Chin et al. | |
| 7,026,026 B2 | 4/2006 | Ferrera et al. | |
| 7,029,732 B2 | 4/2006 | Wang et al. | |
| 7,074,206 B2 | 7/2006 | Lee et al. | |
| 7,112,357 B2 | 9/2006 | Miller et al. | |
| 7,147,817 B1 | 12/2006 | Lim et al. | |
| 7,195,638 B1 | 3/2007 | Sridharan | |
| 7,335,185 B2 | 2/2008 | Tang et al. | |
| 2002/0018866 A1 | 2/2002 | Lee et al. | |
| 2002/0165523 A1 | 11/2002 | Chin et al. | |
| 2003/0009151 A1 | 1/2003 | Wang | |
| 2003/0139762 A1 | 7/2003 | Lee | |
| 2004/0064130 A1 | 4/2004 | Carter | |
| 2004/0131808 A1 | 7/2004 | Schoenle et al. | |
| 2004/0170782 A1 | 9/2004 | Wang et al. | |
| 2004/0173935 A1 | 9/2004 | Lim et al. | |
| 2004/0191443 A1 | 9/2004 | Hamlin | |
| 2005/0043679 A1 | 2/2005 | Devens et al. | |
| 2005/0124976 A1 | 6/2005 | Douglas et al. | |
| 2005/0131445 A1 | 6/2005 | Holman et al. | |
| 2005/0186370 A1 | 8/2005 | Hamilton et al. | |
| 2005/0228429 A1 | 10/2005 | Burgmeier et al. | |
| 2005/0238833 A1 | 10/2005 | Wang et al. | |
| 2005/0277878 A1 * | 12/2005 | Lee | 604/103.04 |
| 2006/0165926 A1 | 7/2006 | Weber | |
| 2007/0060863 A1 | 3/2007 | Goeken et al. | |
| 2007/0142771 A1 | 6/2007 | Durcan | |
| 2007/0167973 A1 | 7/2007 | Stupecky et al. | |
| 2007/0191813 A1 * | 8/2007 | Chen | 604/524 |
| 2007/0240817 A1 | 10/2007 | Strong et al. | |
| 2008/0065188 A1 | 3/2008 | Pallazza | |
| 2008/0262470 A1 | 10/2008 | Lee et al. | |
| 2009/0264822 A1 * | 10/2009 | Johnson | 604/103.07 |
| 2010/0010439 A1 * | 1/2010 | Burgmeier et al. | 604/96.01 |

FOREIGN PATENT DOCUMENTS

| | | |
|---|---|---|
| EP | 0962227 | 12/1999 |
| JP | 2005-167638 | 6/2005 |
| WO | WO99/13924 | 3/1999 |
| WO | 0151115 | 7/2001 |
| WO | 0236196 A1 | 5/2002 |
| WO | 2005021083 | 3/2005 |
| WO | 2006126311 | 11/2006 |

OTHER PUBLICATIONS

U.S. Appl. No. 12/478,929, filed Jun. 5, 2009.

U.S. Appl. No. 12/324,425, filed Mar. 4, 2011 Non-Final Office Action.

U.S. Appl. No. 12/478,929, filed Mar. 4, 2011 Final Office Action.

U.S. Appl. No. 12/478,929, filed Dec. 9, 2010 Response to Non-Final Office Action.

U.S. Appl. No. 12/478,929, filed Jul. 9, 2010 Non-Final Office Action.

International Search Report for PCT/US2010/037313; International Filing Date: Jun. 3, 2010.

U.S. Appl. No. 12/324,425, filed Jun. 6, 2011 Response to Non-Final Office Action.

U.S. Appl. No. 12/478,929, filed Jul. 18, 2011 Request for Continued Examination (RCE).

* cited by examiner

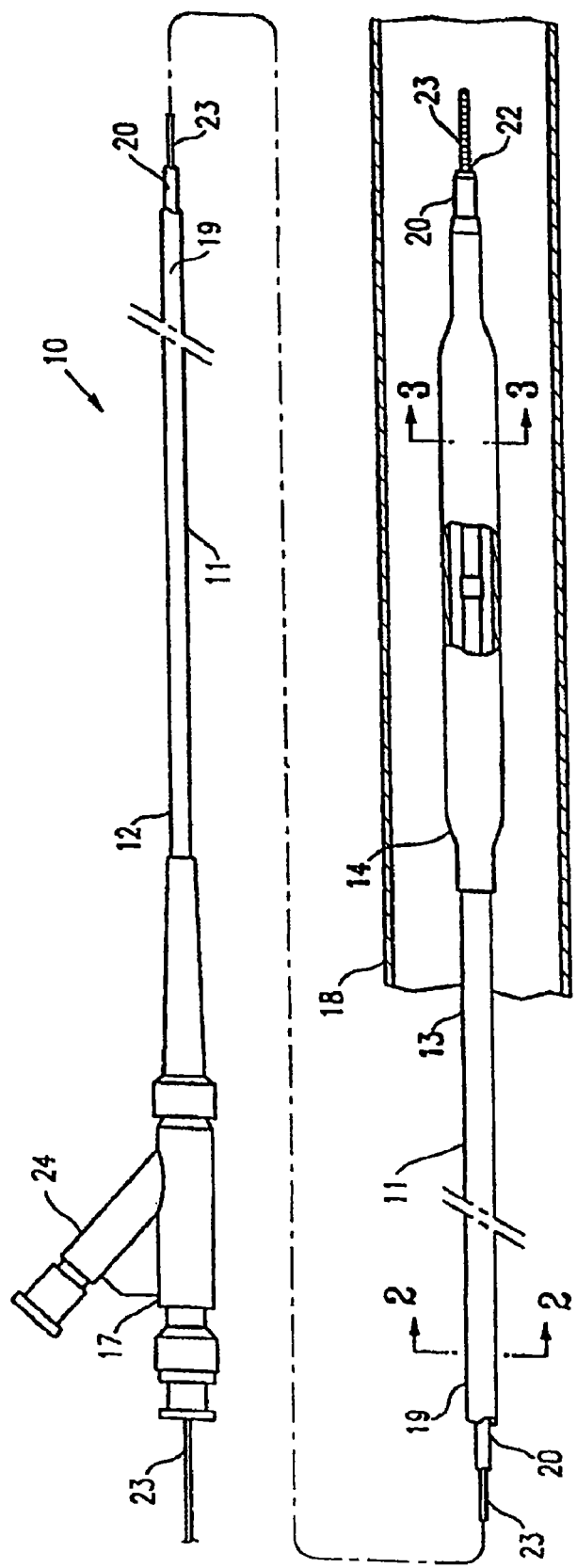
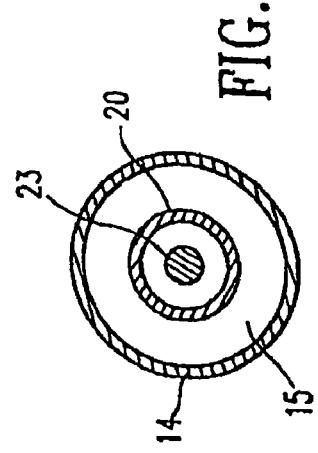

ROBUST MULTI-LAYER BALLOON

CROSS-REFERENCES TO RELATED APPLICATIONS

This application is a continuation-in-part of commonly owned U.S. patent application Ser. No. 12/324,425 entitled "Low Compliant Catheter Tubing" filed Nov. 26, 2008, for which priority is claimed, and the contents of which are fully incorporated herein by reference.

BACKGROUND

The invention relates to the field of intravascular catheters, and more particularly to a balloon catheter or other catheter component, such as a guidewire enclosure, that would benefit from the properties of the materials disclosed herein.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not over expand the artery wall. The rate of expansion of the balloon for a given pressure is an important consideration in the design of the dilation catheter, as greater than anticipated expansion of the balloon against the vessel wall can cause trauma to the vessel wall. After the balloon is finally deflated, blood flow resumes through the dilated artery and the dilatation catheter can be removed from the patient's artery.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons, balloon characteristics such as strength, flexibility and compliance must be tailored to provide optimal performance for a particular application. Angioplasty balloons preferably have high strength for inflation at relatively high pressure, and high flexibility and softness for improved ability to track the tortuous anatomy. The balloon compliance is chosen so that the balloon will have a desired amount of expansion during inflation. Compliant balloons, for example balloons made from materials such as polyethylene, exhibit substantial stretching upon the application of tensile force. Noncompliant balloons, for example balloons made from materials such as PET, exhibit relatively little stretching during inflation, and therefore provide controlled radial growth in response to an increase in inflation pressure within the working pressure range. However, noncompliant balloons generally have relatively low flexibility and softness, making it more difficult to maneuver through various body lumens. Heretofore the art has lacked an optimum combination of strength, flexibility, and compliance, and particularly a low to non-compliant balloon with high flexibility and softness for enhanced trackability.

Another issue of concern in the use of balloons such as catheter balloons described above is the phenomena of shredding. Balloons are designed so that if a failure occurs, the failure is along the longitudinal axis rather than the circumferentially. This is because a failure balloon with a longitudinal failure can still be withdrawn from the patient's vascular, whereas a circumferential failure could result in the distal portion of the balloon becoming detached from the proximal portion, making retrieval problematic. Therefore, any rupture of the balloon is designed to propagate along the length of the balloon. To accomplish this disposition to tear axially, the balloon is imparted with a longitudinal elongation or orientation of the polymer chains that form the balloon's material. Because the stretching of the tubing in the axial direction is predominant over the radial orientation, the molecular chains of the polymer become stretched or elongated in the axial direction. This orientation creates a disposition for tears or shredding in the balloon to propagate along the longitudinal direction.

This predisposition to fail in the axial direction sometimes leads to premature failure, especially during the handling or cleaning process. When the balloon fails, typically strands of balloon material lift and separate from the body of the balloon, and these strands can break away or cause defects in the balloon that can fail during pressurization. Also, the balloon can fail as it is being inflated. Shredding is not limited to elongate strands and may include flakes, chunks, pits, and other discontinuities in the balloon. These defects raise two concerns: (1) that the separated portions of the balloon may become dislodged in use, entering the patient's blood stream and causing blockage, infection, or other issues; and (2) the balloon may rupture prematurely along the defects due to the loss of structural integrity. Therefore, a solution to the problem of balloon shredding is needed. One can reduce the propensity for shredding by decreasing the axial orientation of the blow molded balloon by thermally relaxing the outer layer while maintaining high axial and radial orientation of the inner layer, thus maintaining desired balloon properties. To reduce the axial orientation of the outer layer only, the outer layer is selected to have a relaxation temperature (glass transition temperature or melting temperature) that is lower than the relaxation temperature of the inner layer.

Another issue arises in the formation of the balloon, i.e. the "blowing" process. In a single layer balloon of a semi-crystalline polymer such as Pebax 72D, the modulus of elasticity drops off directly with an increase in temperature. At temperatures where the blowing process occurs, the modulus of elasticity is such that premature rupture frequently occurs, resulting in loss of product. To avoid premature rupture during the blowing process, a multi-layer or blended balloon is formed having a first material of one polyamide having a Shore D durometer value of greater than 77 such as amorphous polymers (e.g., Grilamid TR55) and a second semi-crystalline material of a lower Shore D durometer value, preferably less than 73D, such as Pebax 72D, Pebax 70D, Pebax 63D or Pebax 55D. The co-extrusion or blended material facilitate the blowing process by making the formation more controllable and the blowing procedure can occur at higher temperatures without premature rupture. The inclusion of the amorphous component provides enhanced modulus to the overall balloon, which allows expansion under higher pressures and temperatures without premature rupture.

Another issue arises when the balloon catheter is used as a stent delivery device. Stent needs to be securely mounted on the folded balloon so as not to dislodge during delivery of the stent to the target lesion. Typically a stent is crimped onto a folded balloon at an elevated temperature. In the case of a single layer balloon catheter having high melting temperature such as polyamide or copolyamide, to make the balloon soft enough to imbed the struts of the stent, one is limited on temperature at which the balloon can be exposed due to potential for causing mechanical damage by the stent struts. Having a balloon comprised of an amorphous outer layer such as polyamide having a Shore D durometer value of greater than 77 (e.g., Grilamid TR55) and inner layer a second semi-crystalline material of a lower Shore D durometer value, preferably less than 73D, such as Pebax 72D, Pebax 70D, Pebax 63D or Pebax 55D, allows stent crimping at lower temperatures due to lower glass transition temperature of amorphous outer layer when compared with the melting temperature of semi-crystalline inner layer.

SUMMARY OF THE INVENTION

The softness and flexibility of a balloon is a function of the flexural modulus of the polymeric material of the balloon, so that a balloon material having a higher Shore D durometer hardness, which yields a stronger and stiffer balloon, has a higher flexural modulus. Conversely, a balloon material having a lower Shore D durometer hardness, which thus provides a soft and flexible balloon, has a lower flexural modulus. The present invention is directed to a shredding-resistant, high stent retention catheter balloon formed with a combination of at least two polyamides, a first amorphous material having lower glass transition temperature and a second semi-crystalline material having higher melting temperature than the glass transition temperature of the first amorphous material.

The balloon can be made from a blend of the two polyamides, or a co-extrusion of the two polyamides with an inner layer and an outer layer. The first amorphous polyamide has a Shore D durometer hardness of more than 77D, and can be preferably selected from various transparent amorphous nylons having segment such as an aliphatic segment, an aromatic segment, or a cycloaliphatic segment. The second semi-crystalline polyamide or copolyamide has a lower durometer hardness than the first polyamide, and preferably less than 73D, and can be a block copolymer of nylon and polytetramethylene oxide (i.e. a copolyamide). Both first and second polyamides or copolyamides preferably have the same amide block or segment, e.g. nylon 12, nylon 11, or nylon 6,6.

Where blended, the ratio of the high hardness polyamide to low hardness may preferably have at least sixty percent (60%) low hardness polyamide and forty percent (40%) high hardness polyamide, and more preferably eighty percent (80%) low hardness polyamide and twenty percent (20%) high hardness polyamide, and even more preferably ninety percent (90%) or more of the low hardness polyamide and ten percent (10%) or less of the high hardness polyamide. When co-extruded, the layer thickness of first amorphous polyamide may preferably be less than 20% of the total wall thickness of the extruded tubing.

The low hardness polyamide or copolyamide is typically semi-crystalline having crystalline region and amorphous region. The amorphous region generally has a lower density than the crystalline region and generally has lower modulus, resulting in higher compliance in the amorphous region compared to crystalline region. This higher compliance in the amorphous region affects the overall modulus of the material and causes the material to be more compliant. If amorphous region can be reinforced by a higher modulus compatible material, the overall strength and modulus can be increased and compliance can be decreased. The present invention creates a balloon where the amorphous region of the lower durometer semi-crystalline polyamide or copolyamide is reinforced by adding small amounts of a higher modulus amorphous material, thereby delaying the response of the amorphous region and increasing the overall modulus and strength of the material.

The preferred high hardness material is a new nylon referred to as transparent amorphous nylon, such as selected nylon 12. The transparent amorphous nylon preferably has either an aliphatic segment, an aromatic segment, or a cycloaliphatic segment.

The balloon of the invention is formed by extruding a tubular product formed from the blend of the first polymeric component and at least a second polymeric component. Alternatively, the two polymeric components can be co-extruded to create a tubing having an outer layer and an inner layer of the two materials. In a presently preferred embodiment, the balloon is formed by expanding an extruded tubular product in a balloon mold. Axial tension may be applied to the balloon during expansion, and the balloon may be cooled under pressure and tension between blowing steps. In one embodiment, the balloon is formed by expanding the extruded tubular product in a series of successively larger balloon molds.

Various designs for balloon catheters well known in the art may be used in the catheter system of the invention. For example, conventional over-the-wire balloon catheters for angioplasty or stent delivery usually include a guidewire receiving lumen extending the length of the catheter shaft from a guidewire port in the proximal end of the shaft. Rapid exchange balloon catheters for similar procedures generally include a short guidewire lumen extending to the distal end of the shaft from a guidewire port located distal to the proximal end of the shaft.

A co-extruded balloon can also be used to overcome the problem of shredding of the balloon during use. The co-extruded balloon comprises an outer layer and at least one inner layer, and the two layers will have an axial orientation of the polymer chains due to the blowing process. By selecting the material of the outer layer to have a glass transition temperature below the temperature of the mold during the blowing process, thermal relaxation can be imparted on the outer layer by the heated mold. This thermal relaxation will cause the elongation of the polymer chains to retract and become less oriented. The inner layer, which is made of a material that has a glass or melting temperature above the mold's temperature during forming, will not undergo thermal relaxation and will maintain its high axial orientation. Because the outer layer is more amorphous, there is greater cohesion and the outer layer will have a lower propensity for separation, i.e., shredding, as the balloon is expanded or contracted.

Such a multi-layer balloon will also provide the additional benefit of better stent retention in a stent delivery application due to better adhesion characteristics of the outer layer. That is, if the outer layer is at or above its glass transition temperature and therefore in a softened state, it will be more receptive to attachment of a stent by crimping or other methods that involve penetration of the material. The multilayer balloon will also tend to exhibit higher hoop strength compared to single layer balloons from semi-crystalline polymers due to fewer surface defects and increased strength of the outer layer's materials. These and other advantages of the invention will become more apparent from the following detailed description of the invention and the accompanying exemplary drawings.

A balloon with a higher Shore D value and a lower Shore D value will also contribute to fewer premature ruptures during the blowing process, where the modulus of elasticity contribution from the high Shore D component (either co-extrusion or blended) at an elevated temperature allows the balloon to be blown at higher pressures and temperatures over a single component material of low to medium Shore D hardness.

BRIEF DESCRIPTION OF THE DRAWINGS

FIG. 1 is an elevated view partially in section of a balloon catheter which embodies features of the invention, showing the balloon in an expanded state;

FIG. 2 is a transverse cross sectional view of the balloon catheter of FIG. 1 taken along lines 2-2;

FIG. 3 is a transverse cross sectional view of the balloon catheter of FIG. 1 taken along lines 3-3.

DETAILED DESCRIPTION OF THE PREFERRED EMBODIMENTS

Figure 4:
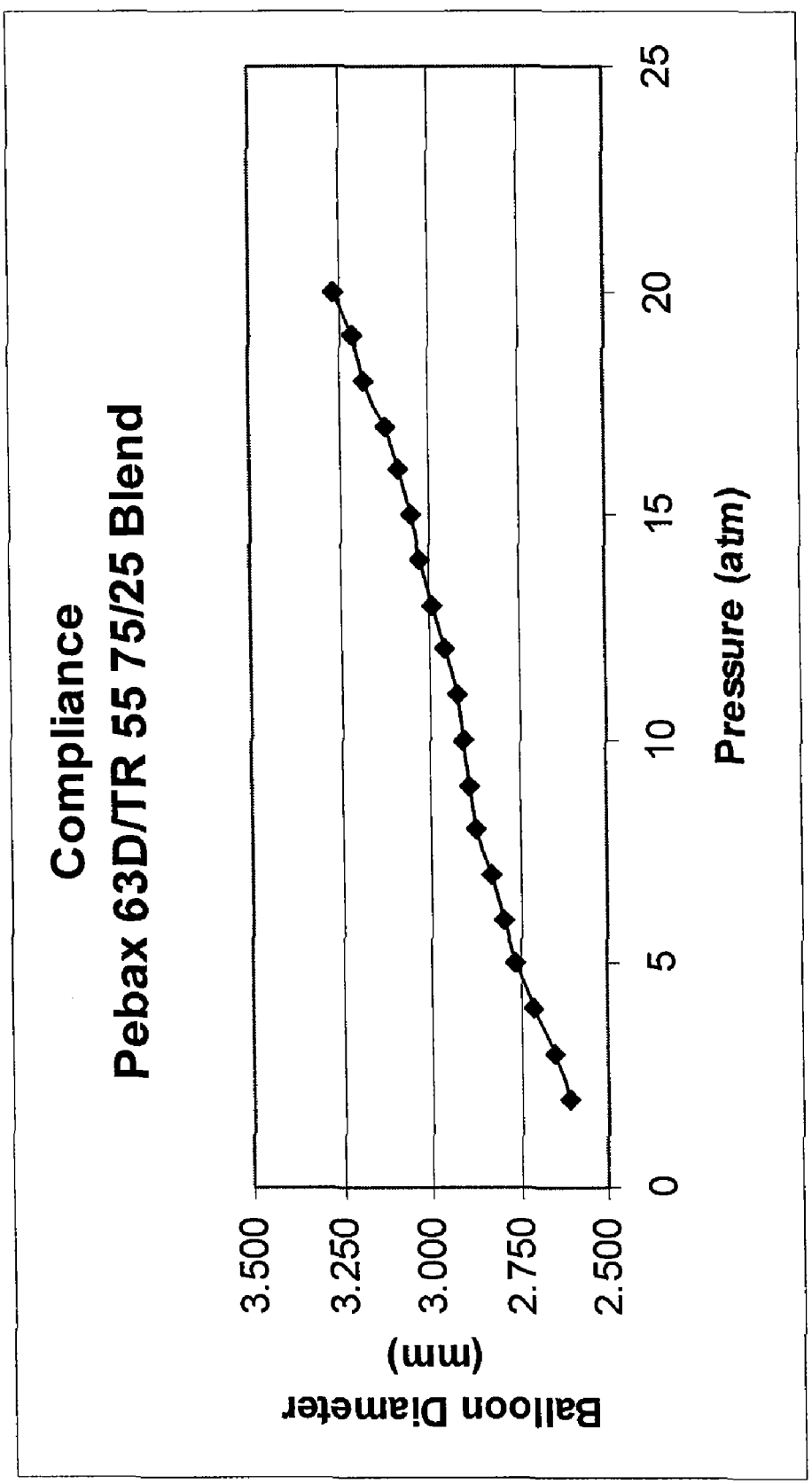
FIG. 4 is a graph of the compliance of the catheter balloon using a first preferred blend of materials.

In angioplasty balloons, an object is to apply a high pressure to the interior wall of the lumen to compress the plaque and/or to fully expand the stent. This relies on a robust balloon with a sturdy out wall and a high pressure capability. The compliance of the balloon, i.e., the expansion of the balloon as a function of internal pressure, is preferably low or flat to more accurately control the amount of pressure applied to the arterial wall. However, the deliverability of the balloon is also a factor, especially where tortuous body lumens are involved. Stiff balloons (i.e., high modulus materials) tend to have poor flexibility and lack the maneuverability to navigate the various body lumens, and thus make poor choices for catheter balloons. Conversely, flexible balloons (low modulus materials) that have high compliance are poorly suited to apply a precise known pressure on the arterial wall due to a high expansion rate per applied pressure. The goal is thus to increase the rupture strength by adding the high modulus material such as nylon to the softer polyamide material.

Soft polyamide materials such as Pebax® are semi-crystalline polymers and usually include an amorphous segment. The amorphous segment has a lower density than the crystalline structure and thus is weaker in general than crystalline segments. If the amorphous segment can be reinforced by adding a small amount of a higher modulus material the response of the amorphous segment can be delayed and the overall strength of the material can be strengthened. The high modulus material preferably has a Shore D durometer hardness of 77D or more. Suitable materials include transparent amorphous nylon such as nylon 12, and more preferably a nylon 12 with an aliphatic segment, an aromatic segment, or a cycloaliphatic segment. These nylons are transparent amorphous because they are essentially amorphous, lacking the crystalline structure of other more conventional nylon 12. The aliphatic segment, aromatic segment, or cycloaliphatic segment does not crystallize with the main chain, disrupting the formation of longer crystalline chains in the polymer. The amorphous segment of the transparent amorphous nylon 12 combines with the amorphous segment of the Pebax to strengthen the Pebax by enhancing the weakest link in the chain, thereby increasing the overall strength of the polymer. The benefit is realized with small amounts of the high modulus material, with as little as 40% to 10% of the high modulus material combining with 60% to 90% of the low strength Pebax.

FIG. 1 illustrates a balloon catheter which embodies features of the invention. The catheter 10 of the invention generally comprises an elongated catheter shaft 11 having a proximal section, 12 a distal section 13, an inflatable balloon 14 formed of a blend of polymeric materials on the distal section 13 of the catheter shaft 11, and an adapter 17 mounted on the proximal section 12 of shaft 11. In FIG. 1, the catheter 10 is illustrated within a patient's body lumen 18, prior to expansion of the balloon 14.

In the embodiment illustrated in FIG. 1, the catheter shaft 11 has an outer tubular member 19 and an inner tubular member 20 disposed within the outer tubular member and defining, with the outer tubular member, inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19.

FIGS. 2 and 3 show transverse cross sections of the catheter shaft 11 and balloon 14, respectively, illustrating the guidewire receiving lumen 22 of the guidewire's inner tubular member 20 and inflation lumen 21 leading to the balloon interior 15. The balloon 14 can be inflated by radiopaque fluid introduced at the port in the side arm 24 into inflation lumen 21 contained in the catheter shaft 11, or by other means, such as from a passageway formed between the outside of the catheter shaft and the member forming the balloon, depending on the particular design of the catheter. The details and mechanics of balloon inflation vary according to the specific design of the catheter, and are well known in the art.

Non-compliant or low-compliant balloon 14 is formed of a blend of a first polyamide having a Shore D durometer hardness greater than 77D and a copolyamide of lower durometer hardness, preferably less than 73D. A preferred polyamide having a Shore D durometer hardness greater than 77D is an amorphous polyamide such as EMS TR 55 (transparent amorphous nylon 12), Arkema Rilsan G110 (transparent amorphous nylon 12), or Cristamid MS 110 (transparent amorphous nylon 12). The polyamide is preferably includes a cycloaliphatic segment, an aromatic segment, or an aliphatic segment. Such polyamides are also referred to as transparent polyamide. The preferred copolyamide material for forming the polymeric blend for the balloon is Pebax, and more preferably Pebax 72D, Pebax 70D, Pebax 63D, or Pebax 55D. Alternatively, the copolyamide of lower durometer hardness is preferably a block copolymer of nylon 12 and polytetramethylene oxide.

The flexural modulus of the polyamide is preferably greater than 1700 MPa (240,000 psi) and the flexural modulus of the copolyamide is less than 850 MPa (120,000 psi). The tensile strength at break of both polyamides is at least 50 MPa, and elongation at break of both polyamides is at least 150%.

In a presently preferred embodiment, the balloon of the invention is formed by blow molding an extruded tubular product formed of a blend of the first and second polyether block amide polymeric materials. The extruded tubular product is expanded to the final working diameter of the balloon in a balloon mold. The balloon may be heat set in the mold. In one alternate embodiment, the balloon is blown in a series of successively larger balloon molds. Thus, the extruded tubular product is placed in a first mold and the outer diameter of the tubular product is expanded at elevated pressure and temperature to a first outer diameter. The balloon is then placed in a second, larger mold, and expanded at elevated pressure and temperature to a second outer diameter larger than the first outer diameter. The number of successively larger molds used to expand the balloon may vary depending on the balloon material and size. To form a 3.0 mm outer diameter (OD) balloon, the tubular member is expanded in a first mold to an OD of about 2.0 to about 2.5 mm, and then expanded in a second mold to the working diameter of 3.0 mm. Preferably, axial tension is applied to the balloon during expansion, and the balloon is cooled in the mold, under pressure and tension, between blowing steps. However, the balloon of the invention is preferably produced by conventional techniques for producing catheter inflatable members in which the extruded tubular product is expanded in a single mold to the working diameter.

The balloon 14 has sufficient strength to withstand the inflation pressures needed to inflate the balloon. The tensile strength of an American Standard Testing Method (ASTM) "dog-bone" sample cut from a compression molded sheet of material is at least about 8,000 psi to about 9,000 psi. The hoop strength, e.g. the product of the burst pressure and the balloon diameter, divided by two times the balloon wall thickness, of a 3.0 mm balloon of the invention is about 22,000 psi to about 32,000 psi.

The catheter shaft will generally have the dimensions of conventional dilatation or stent deploying catheters. The length of the catheter 10 may be about 90 cm to about 150 cm, and is typically about 135 cm. The outer tubular member 19 has a length of about 25 cm to about 40 cm, an outer diameter (OD) of about 0.039 in to about 0.042 in, and an inner diameter (ID) of about 0.032 in. The inner tubular member 20 has a length of about 25 cm to about 40 cm, an OD of about 0.024 in and an ID of about 0.018 in. The inner and outer tubular members may taper in the distal section to a smaller OD or ID.

The length of the compliant balloon 14 may be about 1 cm to about 4 cm, preferably about 0.8 cm to about 4.0 cm, and is typically about 2.0 cm. In an expanded state, at nominal pressure of about 8 to about 10 atm, the balloon diameter is generally about 0.06 in (1.5 mm) to about 0.20 in (5.0 mm). and the wall thickness is about 0.0006 in (0.015 mm) to about 0.001 in (0.025 mm), or a dual wall thickness of about 0.025 mm to about 0.056 mm. The burst pressure is typically about 20 to 26 atm, and the rated burst pressure is typically about 18 atm.

In a presently preferred embodiment, the balloon 14 may include wings, which may be folded into a low profile configuration (not shown) for introduction into and advancement within the patient's vasculature. When inflating the balloon to dilate a stenosis, the catheter 10 is inserted into a patient's vasculature to the desired location, and inflation fluid is delivered through the inflation lumen 21 to the balloon 14 through the inflation port 24. The semi-compliant or noncompliant balloon 14 expands in a controlled fashion with limited radial expansion, to increase the size of the passageway through the stenosed region. Similarly, the balloon has low axial growth during inflation, to a rated burst pressure of about 14 atm, of about 5 to about 10%. The balloon is then deflated to allow the catheter to be withdrawn. The balloon may be used to deliver a stent (not shown), which may be any of a variety of stent materials and forms designed to be implanted by an expanding member, see for example U.S. Pat. No. 5,514,154 (Lau et al.) and U.S. Pat. No. 5,443,500 (Sigwart), incorporated herein in their entireties by reference.

Example 1

A blended composition of 75% Pebax 63D and 25% EMS TR 55 (transparent amorphous nylon) was constructed into ten sample catheter balloons according to the present invention, which produced an average working pressure range of eight to nine atmospheres for a 2.75 mm balloon. At five atmospheres, the balloon is about 2.75 mm (nominal diameter) and at thirteen atmospheres the balloon has grown radially roughly 0.25 mm to 3.00 mm (quarter size diameter). As shown in FIG. 4, this results in a compliance performance that is flatter in the operating range of the balloon, a desired characteristic. The balloon in Example 1 has a compliance of about 0.023 mm/atm between 5 atmospheres and 18 atmospheres, i.e., from nominal to the rated burst pressure of the balloon, where the nominal pressure is the pressure required to expand the balloon to its working diameter, and the rated burst pressure, calculated from the average rupture pressure, is the pressure at which 95% of the balloons can be pressurized to without rupturing.

The benefit of the present invention is blending amorphous (transparent amorphous) nylon to Pebax to reinforce the amorphous region (due to exclusion into amorphous region during crystallization) of semi crystalline region of Pebax or nylon. This results in a higher tensile strength (~11,000 psi) compared to nylon 12 or Pebax (7,500~8,200 psi) to yield a higher rupture balloon with same wall thickness; higher flexural modulus (~270,000 psi) compared to nylon 12 or Pebax (60,000~230,000 psi) to produce a flatter compliance balloon with same wall thickness; enhanced dimensional stability during shelf storage due to the higher glass transition temperature (155° C.) compared to nylon 12 or Pebax (45~55° C.); and lower processing temperature facilitating the thermal bonding process.

U.S. Pat. No. 7,074,206 co-invented by the inventor of the present invention and assigned to the assignee of the present application, incorporated fully herein by reference, discloses a catheter balloon where Pebax 70D is blended with a softer Pebax 63D to add flexibility to the Pebax 70D balloon. Approximately 40% by weight of the higher modulus Pebax 70D is blended with 60% by weight of the softer Pebax, to yield a balloon with a working pressure range of 6 atm (pressure at quarter size-nominal pressure). The present invention, for example the blend described above, shows that, with 25% TR55 (amorphous nylon) blended into Pebax 63D, the working pressure range for a 2.75 mm balloon is now 8~9 atm (nominal pressure 5 atm and quarter size at 13~14 atm), with a flatter compliance. Thus, the present invention yields a stronger balloon with a flatter compliance without sacrificing flexibility.

In addition to balloons, the blended composition has usefulness as other parts of the catheter, such as the guidewire enclosure 20 of FIGS. 1-3. The inner member of the multi-layered tubing can have a lubricious inner layer (HDPE, UHMWPE, and the like) with bonding mid layer and polymer blend outer layer. Like the catheter balloon, the blend is comprised of one polymer having a Shore D durometer greater than 77 and another polymer having lower durometer, preferably less than 73D. Both polyamides preferably have same amide block or segment, i.e. one type of amide (nylon) block, solely comprised of nylon 12, nylon 11, nylon 6, or nylon 6, 6 but not combination of these.

The polyamide having Shore D durometer greater than 77D is preferably amorphous polyamide selected from polyamide such as EMS TR 55 (transparent amorphous nylon 12), Arkema Rilsan G110 (transparent amorphous nylon 12), or Cristamid MS 110 (transparent amorphous nylon 12). This polyamide is preferably a copolyamide comprising cycloaliphatic, and/or aromatic, and/or aliphatic segment. The other copolyamide of lower durometer is preferably a block copolymer of nylon 12 and polytetramethylene oxide, such as Pebax 72D, Pebax 70D or Pebax 63D.

The high durometer polymer serves to increase resistance to collapse of the tubing and provides enhanced pushability while the lower durometer polymer provides flexibility and kink resistance. Although it is preferred to have blends of high miscibility, the blend ratio is such that the lower durometer polymer forms a "virtual" continuous phase while the higher durometer polymer forms "virtual" reinforcement.

Figure 5:
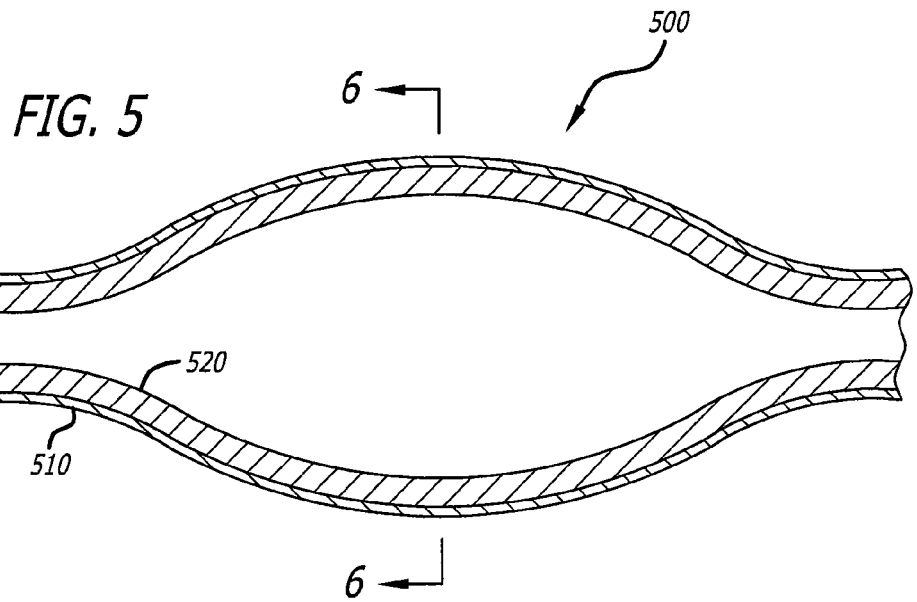
FIG. 5 is a first cross-sectional view of a multi-layer balloon having a shredding resistant outer layer.
Figure 6:
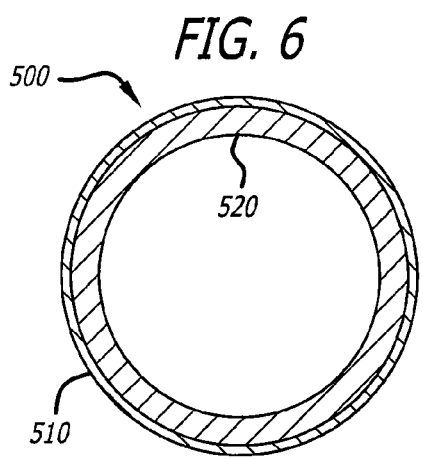
FIG. 6 is a second cross-sectional view of a multi-layer balloon having a shredding resistant outer layer.
Figure 7:
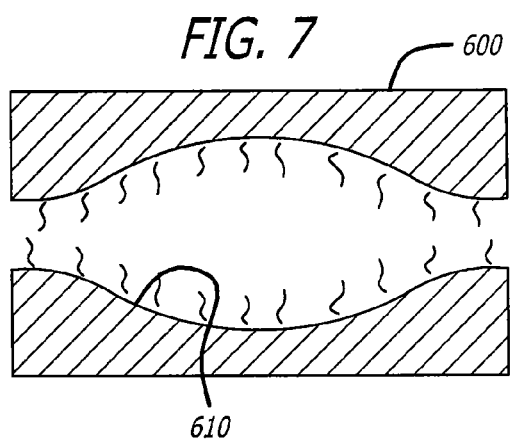
FIG. 7 is a heated balloon mold used to make the balloon of FIG. 5.
Figure 8A:
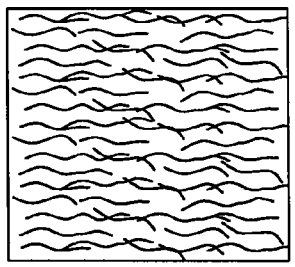
FIGS. 8a and 8b are schematic representations of enlarged views of the molecular chains in the outer layer of the balloon of FIG. 5 before and after thermal relaxation, respectively.
Figure 8B:
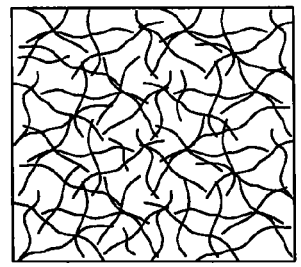

A balloon designed to resist shredding and premature rupture during blowing is shown in FIGS. 5 and 6, and can preferably be formed of a material with a common structure such as polyamide. The multi-layer balloon 500 has an outer layer 510 and an inner layer 520, which is blown in a mold 600 such as that shown in FIG. 7. During the blowing process, the outer layer 510 comes in contact with the heated inner surface 610 of the mold 600. This process may be repeated in steps using gradually larger molds to expand the balloon 500 to the desired size and dimension. To create an outer surface that resists shredding, the outer layer is selected from a material that has a glass transition temperature that is lower than the temperature on the inner surface 610 of the mold 600 during the blowing process. This intimate contact between the heated mold and the outer surface 510 of the balloon 500 will cause thermal relaxation of the polymer strands in the outer layer 510. This is characterized by FIGS. 8a and 8b, which represents the polymer chains before relaxation with a high axial orientation and after relaxation with less axial orientation. The material post-relaxation (FIG. 8b) will exhibit a reduced tendency to shred or separate due to the more intertwined nature of the polymer chains. The inner layer 520 of the balloon, which has a higher glass transition temperature and does not come in contact with the mold 600, will continue to possess a high axial orientation and behave to resist circumferential failure of the balloon. The inclusion of the outer layer of amorphous polymer also increases the modulus of elasticity, particularly in the 120° C. to 150° C. range where balloon formation can occur. This is due to the flatter slope of the amorphous nylons when comparing the modulus versus temperature curves as compared with the softer polymers such as Pebax 72D or softer. This can also be incorporated into a blended composition where the two or more polyamides are blended prior to the blowing operation.

An example of the multi-layer shred resistant balloon combines an outer layer of amorphous EMS TR 55 (transparent amorphous nylon 12), which has a glass transition temperature of approximately 155° C., with an inner layer of a highly crystalline or semi-crystalline polymer such as Pebax 72D having a melting temperature of approximately 172° C. As the balloon is blown, if the mold is heated to 120° C. to 150° C. under pressure, the molecular chains in the outer layer of the balloon will undergo thermal relaxation and the stretched chains will relax and reorient in a less axial pattern while the crystalline or semi-crystalline inner layer will maintain its high axial orientation. The relaxed outer layer will have a lower propensity to shred due to the more general orientation of the polymer chains.

The amorphous outer layer of the catheter balloon can be comprised of an amorphous polyamide selected from polyamide such as EMS TR 55 (transparent amorphous nylon 12), Arkema Rilsan G110 (transparent amorphous nylon 12), Cristamid MS 110 (transparent amorphous nylon 12), polyamide 11, polyamide 6, or polyamide 6,6. This polyamide is preferably a copolyamide comprising cycloaliphatic, and/or aromatic, and/or aliphatic segment. The inner layer can be comprised of a crystalline or semi-crystalline copolymer of nylon 12 and polytetramethylene oxide, such as Pebax 72D or Pebax 70D. Other materials are also contemplated, as long as the outer layer has a glass transition or melting temperature that is preferably lower than, or at least approximately equal to, the surface temperature of the mold during the blowing or forming process of the balloon.

We claim:

1. A balloon catheter, comprising:
    a shaft having a proximal end, a distal end, and an inflation lumen extending therein; and
    a balloon on the shaft which has an interior in fluid communication with the inflation lumen, the balloon having an outer layer and an inner layer, the outer layer comprising a material having a first transition temperature, and the inner layer comprising a material having a second transition temperature, the second transition temperature being higher than the first transition temperature;
    wherein the balloon is formed at a temperature between said first and second transition temperatures such that the outer layer has a first degree of axial orientation of polymer strands and the inner layer has a second degree of axial orientation of polymer strands, the second degree of axial orientation being greater than the first degree of axial orientation.

2. The balloon catheter of claim 1 wherein the first transition temperature is a glass transition temperature.

3. The balloon catheter of claim 1 wherein the second transition temperature is a melting temperature.

4. The balloon catheter of claim 1 wherein the temperature that the balloon is formed is between 120° C. and 150° C.

5. The balloon catheter of claim 1 wherein the temperature that the balloon is formed at thermally relaxes polymer chains in the outer layer to reduce from a high degree of axial orientation to the first degree of axial orientation.

6. The balloon catheter of claim 1 wherein the inner layer and the outer layer comprise layers of the balloon.

7. The balloon catheter of claim 1 wherein the outer layer is amorphous polymer.

8. The balloon catheter of claim 1 wherein the inner layer is semi-crystalline polymer.

9. The balloon catheter of claim 1 wherein the inner layer and the outer layer are both made of a polyamide.

10. The balloon catheter of claim 9 wherein the polyamide is selected from a group comprising polyamide 12, polyamide 11, polyamide 6, and polyamide 6,6 or copolyamides of polyamide 12, polyamide 11, polyamide 6, and polyamide 6,6.

11. The balloon catheter of claim 1 wherein the outer layer is comprised of a copolymer of aliphatic type with aromatic type.

12. The balloon catheter of claim 1 wherein the outer layer is comprised of a copolymer of aliphatic type with cycloaliphatic type.

13. The balloon catheter of claim 1 wherein the inner layer is comprised of a copolymer of polyamide and polytetramethylene oxide.

14. The balloon catheter of claim 1 wherein the balloon is formed by blow molding.

15. The balloon catheter of claim 1 wherein the first transition temperature is a glass transition temperature and the second transition temperature is a glass transition temperature.

16. A balloon catheter, comprising:
   a shaft having a proximal end, a distal end, and an inflation lumen extending therein; and
   a balloon on the shaft which has an interior in fluid communication with the inflation lumen, the balloon having an outer layer and an inner layer, the outer layer comprising a material having a first glass transition temperature, and the inner layer comprising a material having a second glass transition temperature higher than the first glass transition temperature;
   wherein the balloon is blow molded at a temperature higher than first glass transition temperature and lower than the second glass transition temperature, such that the outer layer has a first degree of axial orientation of polymer strands and the inner layer has a second degree of axial orientation of polymer strands, the second degree of axial orientation being greater than the first degree of axial orientation.

* * * * *